United States Patent
Thaning et al.

(10) Patent No.: US 10,314,927 B2
(45) Date of Patent: Jun. 11, 2019

(54) FORMULATIONS OF METAL COMPLEXES

(71) Applicant: GE HEALTHCARE AS, Oslo (NO)

(72) Inventors: Mikkel Jacob Thaning, Oslo (NO); Andreas Richard Meijer, Oslo (NO)

(73) Assignee: GE HEALTHCARE AS, Oslo (NO)

( * ) Notice: Subject to any disclaimer, the term of this patent is extended or adjusted under 35 U.S.C. 154(b) by 0 days.

(21) Appl. No.: 15/531,430

(22) PCT Filed: Nov. 27, 2015

(86) PCT No.: PCT/EP2015/077961
§ 371 (c)(1),
(2) Date: May 27, 2017

(87) PCT Pub. No.: WO2016/083600
PCT Pub. Date: Jun. 2, 2016

(65) Prior Publication Data
US 2017/0258944 A1  Sep. 14, 2017

(30) Foreign Application Priority Data

Nov. 28, 2014 (GB) .................................. 1421163.5

(51) Int. Cl.
*A61K 49/10* (2006.01)
*A61K 49/18* (2006.01)

(52) U.S. Cl.
CPC ............ *A61K 49/108* (2013.01); *A61K 49/10* (2013.01); *A61K 49/18* (2013.01)

(58) Field of Classification Search
CPC ....... A61K 49/10; A61K 49/18; A61K 49/108
See application file for complete search history.

(56) References Cited

U.S. PATENT DOCUMENTS

| 5,527,688 A * | 6/1996 | Mallia ................ B01L 3/502 424/10.3 |
| 2009/0208421 A1 | 8/2009 | Meyer et al. |

FOREIGN PATENT DOCUMENTS

| EP | 2799090 A2 | 11/2014 |
| WO | 2014114664 A1 | 7/2014 |
| WO | 2016083600 A1 | 6/2016 |

OTHER PUBLICATIONS

International Search Report and the Written Opinion of the International Searching Authority, or the Declaration from International Appl. No. PCT/EP2015/077961, dated Feb. 15, 2016.
Great Britain Search Report from GB Appl. No. GB1421163.5, dated Aug. 13, 2015.

* cited by examiner

*Primary Examiner* — Zohreh A Fay
(74) *Attorney, Agent, or Firm* — Arent Fox LLP

(57) ABSTRACT

The present invention relates to a method of preparation of formulations of gadolinium metal complexes of the macrocyclic chelator DOTA, which further comprise a small excess of free DOTA. The method uses controlled conditions such that excess gadolinium is present as a precipitate of gadolinium oxide, with filtration to remove the excess, prior to the addition of a defined excess of DOTA chelator. Also provided is a method of preparation of MRI contrast agents based on Gd-DOTA.

11 Claims, No Drawings

FORMULATIONS OF METAL COMPLEXES

FIELD OF THE INVENTION

The present invention relates to a method of preparation of formulations of gadolinium metal complexes of the macrocyclic chelator DOTA, which further comprise a small excess of free DOTA. The method uses controlled conditions such that excess gadolinium is present as a precipitate of gadolinium oxide, with filtration to remove the excess, prior to the addition of a defined excess of DOTA chelator. Also provided is a method of preparation of MRI contrast agents based on Gd-DOTA.

BACKGROUND TO THE INVENTION

Metal complexes of lanthanide metals, especially gadolinium, are of interest as MRI contrast agents in the field of in vivo medical imaging. MRI contrast agents based on metal complexes of gadolinium have been reviewed extensively [see e.g. Zhang et al, Curr. Med. Chem., 12, 751-778 (2005) and Aime et al, Adv. Inorg. Chem., 57, 173-237 (2005)].

Free gadolinium ions do, however, exhibit significant toxicity in vivo. U.S. Pat. No. 5,876,695 addresses this problem by including in the formulation of the gadolinium metal complex an additive, which is a 'weak metal chelate complex' such as with calcium. The idea is that the excess 'weak metal chelate complex' will complex efficiently any gadolinium ions which may adventitiously be either liberated or present, and thus improve the safety of the MRI contrast composition.

EP 2513043 B1 discloses a method of preparation of gadolinium metal complexes in which gadolinium is first complexed to a cation exchange resin optionally functionalised with a metal coordinating group. The solid-phase bound gadolinium is subsequently reacted with an aminocarboxylic acid chelating agent to liberate the desired gadolinium complex. Any excess gadolinium remains bound to the solid-phase.

EP 2242515 B9 discloses a process for preparing a liquid pharmaceutical formulation containing a complex of macrocyclic chelate with a lanthanide and a mol/mol amount of free macrocyclic chelate of between 0.002% and 0.4%, said process comprising the following successive steps:

b) preparation of a liquid pharmaceutical composition containing the complex of macrocyclic chelate with a lanthanide, and free macrocyclic chelate that is not under the form of an excipient X[X', L] in which L is the macrocyclic chelate and X and X' are a metal ion, in particular chosen independently from calcium, sodium, zinc and magnesium, and free lanthanide, by mixing a solution of free macrocyclic chelate and of free lanthanide, so as to obtain complexation of the lanthanide by the macrocyclic chelate, the amounts of free macrocyclic chelate and of free lanthanide being such that not all the lanthanide is complexed;

c) measurement in the pharmaceutical formulation obtained in step b) of the concentration of free lanthanide $C_{lan\ 1}$; the concentration of free macrocyclic chelate $C_{ch\ 1}$ being equal to 0;

d) adjustment of $C_{ch\ 1}$ and of $C_{lan\ 1}$ by adding to the formulation obtained in step b) the amount of free macrocyclic chelate necessary, firstly, to complete the complexation of the free lanthanide so as to obtain $C_{lan\ 1}=0$, and, secondly, to obtain $C_{ch\ 1}=C_{t\ ch\ 1}$, wherein $C_{t\ ch\ 1}$ is the target concentration of the free macrocyclic chelate in the final liquid pharmaceutical formulation and is selected in the range of between 0.002% and 0.4% mol/mol, wherein the amount of free macrocyclic chelate in the final liquid pharmaceutical formulation corresponds to the proportion of free macrocyclic chelate relative to the amount of complexed macrocyclic chelate in the final liquid pharmaceutical formulation.

EP 2242515 B9 teaches that the method preferably further includes a prior step a) of determination of the theoretical target concentration of free macrocyclic chelate $C_{t\ ch\ 1}$ in the final liquid pharmaceutical formulation.

US 2012/0082624 A1 discloses a similar process to EP 2242515 B9, except that the pharmaceutical formulation is obtained in powder form.

Both EP 2242515 B9 and US 2012/0082624 A1 stress that, for an industrial scale pharmaceutical manufacturing processes, the addition of 0.1 mol % free macrocyclic chelator is difficult to achieve with the required degree of accuracy by weighing alone. That was ascribed to the 1000-fold difference in amounts of chelator involved, plus the hygroscopic nature of the chelator. The claimed invention, as described above, is to first carry out the metal complexation with an excess of lanthanide metal ion, then secondly to determine accurately the concentration of uncomplexed, excess lanthanide. That determination is subsequently used to calculate exactly how much additional chelator must be added to both complex the excess lanthanide and achieve the desired 0.1% molar excess of macrocyclic chelate.

Reference Example 3 of EP 2242515 B9 includes a laboratory scale preparation which prepares Gd-DOTA by reaction of DOTA (10 g, 25 mmol) with a stoichiometric amount of gadolinium oxide ($Gd_2O_3$, 12.5 mmol) at 80° C. in water at pH 6 to 7. The pH is then adjusted to 5, and residual free gadolinium removed by stirring with a Chelex resin for 2-hours, followed by filtration. EP 2242515 B9 teaches that the Gd-DOTA complex is then precipitated from aqueous ethanol giving an 80% isolated yield of white powder. EP 2242515 B9 does not teach how the method of Reference Example 3 can be adapted to provide the liquid pharmaceutical composition having an excess of macrocyclic chelator in the range 0.002% and 0.4% mol/mol, in particular on an industrial scale.

WO 2014/114664 provides a process for the preparation of Gd-DOTA meglumine (gadoterate meglumine) which first comprises the synthesis of DOTA from cyclen followed by multi-step purification via recrystallisation and both cation and anion exchange chromatography. The purified DOTA is then reacted with $Gd_2O_3$ to give the Gd-DOTA complex, followed by the addition of meglumine to give the desired product.

WO 2014/161925 teaches that, when preparing Gd-DOTA and similar complexes on an industrial scale, it is necessary to assay the moisture content of the chelator prior to use and to correct the molar amounts used accordingly. WO 2014/161925 notes that the moisture content of DOTA varies with the relative humidity conditions.

There is still a need for alternative methods of preparing formulations of lanthanide metal complexes of macrocyclic chelators incorporating an excess of such chelators. The methods should preferably be suitable for pharmaceutical manufacture on an industrial scale, and also be suitable for the provision of MRI contrast agents comprising such formulations.

THE PRESENT INVENTION

The present invention provides a method of preparation of a liquid pharmaceutical formulation, said formulation comprising a gadolinium DOTA complex, together with DOTA in uncomplexed form in an amount in the range 0.002 and 0.4 mol/mol %. Such formulations are useful in the provision of MRI contrast agents.

Then present method avoids the need for the measurement and adjustment steps of the prior art, which is a useful simplification in terms of both time and effort.

The present method instead provides a method whereby first, the Gd-DOTA metal complex is obtained without excess gadolinium ions being present. That is achieved by controlling the reaction conditions such that any excess gadolinium is present as insoluble $Gd_2O_3$ which can be removed by filtration. Furthermore, the Gd-DOTA complex is maintained in aqueous solution, so correction for the moisture content of the complex is unnecessary. Since the process provides an intermediate solution of Gd-DOTA metal complex without free gadolinium ions, the amount of excess DOTA to add to give the desired formulation having a defined excess of free chelator can be calculated readily.

The method of the present invention has the further advantage that it can be carried out on an industrial scale.

DETAILED DESCRIPTION OF THE INVENTION

In a first aspect, the present invention provides a method of preparation of a liquid pharmaceutical formulation, said formulation comprising a meglumine salt of the metal complex Gd-DOTA, together with DOTA in uncomplexed form in an amount in the range 0.002 and 0.4 mol/mol % of said Gd-DOTA complex, said process comprising the following steps:
(i) reaction of either:
  (a) an aqueous solution of a 1:1 molar ratio of DOTA and meglumine with an excess of $Gd_2O_3$, whereby all the DOTA reacts to give Gd-DOTA; or
  (b) an aqueous solution of DOTA with a deficiency of $Gd_2O_3$ at pH 2.0 to 6.0 whereby all the gadolinium reacts to give Gd-DOTA, followed by the addition of meglumine to raise the pH to 6.5 to 8.0, and then addition of an excess of $Gd_2O_3$; or
  (c) an aqueous solution of DOTA with an excess of meglumine at pH 6.5 to 8.0, with an excess of $Gd_2O_3$, whereby all the DOTA reacts to give Gd-DOTA;
whereby (a), (b) or (c) gives a first solution of Gd-DOTA containing excess undissolved $Gd_2O_3$;
(ii) filtration of the first solution from step (i) to remove the excess undissolved $Gd_2O_3$, giving a second solution which comprises Gd-DOTA free from excess $Gd_2O_3$;
(iii) addition of DOTA in uncomplexed form in the range 0.002 and 0.4 mol/mol % to said second solution from step (ii) to give said liquid pharmaceutical formulation;
wherein said DOTA in uncomplexed form is free of coordinated metal ions.

The term "DOTA" is the conventional abbreviation for the macrocyclic chelator 1,4,7,10-tetraazacyclododecane-1,4,7,10-tetraacetic acid, and refers to DOTA itself or a salt thereof:

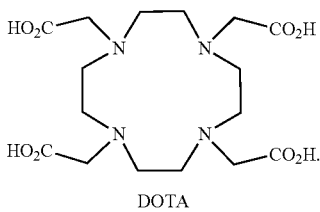

DOTA

DOTA and its' metal complexes in biomedical imaging have been described by Stasiuk and Long [Chem. Comm., 49, 2732-2746 (2013)].

The phrase "DOTA in uncomplexed form" refers to the 'free chelator', i.e. without any coordinated metal ions. Hence, the DOTA in uncomplexed form does not have any coordinated lanthanide or other metal ions, and is thus fully available for subsequent metal complexation. The 'DOTA in uncomplexed form' may contain metal ions in ionic form, such as when present as carboxylate salts of the carboxylic acid metal donor group.

The term "meglumine" has its conventional meaning, and refers to N-methylglucamine The terms "comprising" or "comprises" have their conventional meaning throughout this application and imply that the agent or composition must have the essential features or components listed, but that others may be present in addition. The term 'comprising' includes as a preferred subset "consisting essentially of" which means that the composition has the components listed without other features or components being present.

Suitable solvents for the complexation of step (i) are known in the art [*The Chemistry of Contrast Agents in Medical Magnetic Resonance Imaging*, $2n^d$ Edition, A. Merbach, L. Helm & E. Toth (Eds), Wiley (2013)], and are suitably aqueous. The complexation of gadolinium by macrocyclic chelators (e.g. DOTA) is a multistep process that involves a somewhat stable initial complex that slowly matures to give the final, thermodynamically stable metal complex.

The excess of gadolinium in step (i)(a), or the excess of DOTA in step (i)(b) are obtained by calculation of the molar ratios knowing the stoichiometry of the gadolinium DOTA complex to be a 1:1 complex. The percentage chemical purity of both the gadolinium used and the DOTA are also taken into account.

Gadolinium oxide ($Gd_2O_3$) is insoluble in water, but will hydrolyse at acidic pH to give free gadolinium ions in solution. At neutral pH this hydrolysis has been reported to be non-existent or very slow [Hemmer et al, Adv. Mat. Sci. Eng., 1-15 (2012) doi: 10.1155/2012/748098).

In step (i)(a), an excess of gadolinium oxide is added to a mixture in a 1:1 molar ratio of DOTA and meglumine The DOTA will consume gadolinium oxide and form Gd-DOTA, and the pH will approach a higher pH (pH 6-8) at the end of the complexation, by use of the correct DOTA/meglumine ratio (100:95 to 100:100 molar ratio DOTA/meglumine). Given the higher pH, hydrolysis of insoluble gadolinium oxide is very slow, which allows for subsequent removal of excess gadolinium oxide by filtration.

In step (i)(b), a sub-stoichiometric amount of $Gd_2O_3$ is added to the DOTA at acidic pH. After complete consumption of the gadolinium oxide, meglumine is added to raise the pH to 6.5 to 8.0, followed by an excess of $Gd_2O_3$ (ca. 1 to 5%). This facilitates complete complexation of all the DOTA, while minimising hydrolysis of excess $Gd_2O_3$ (due to the slow kinetics at neutral pH). In this process the high complexation rate at low pH and low hydrolysis rate at elevated pH are both utilised.

In step (i)(c), an excess of meglumine is used leading to a more elevated pH (ca. pH 6.5-8) leading to an even lower degree of hydrolysis of the gadolinium oxide. The alkaline Gd-DOTA-meglumine solution is then neutralised by the addition of a 0.1 mol/% excess DOTA in step (iii), due to the acidity of the DOTA.

The filtration of step (ii) can be achieved by standard methods.

The addition of step (iii) is preferably carried out without a prior, in-process assay of the concentration/amount of free gadolinium in either the first or second solutions. That is because such a step is unnecessary for the present method—the filtration of step (ii) gives the 'second solution' with a known (i.e. effectively zero) concentration of free gadolinium. Hence, the addition of step (iii) is carried out on the basis of a calculated amount of 'DOTA in uncomplexed form' based on an assumed 100% conversion in the complexation reaction of step (i), based on the starting molar amount of DOTA in step (i). That 100% conversion is in accord with what is known in the art on the efficiency of such reactions. The free DOTA can be added either as a solid, or as a solution and preferably as a solution. When a solution of DOTA is prepared in order to carry out step (i), then a most preferred method is to remove a suitable volume fraction from that solution prior to the addition of the gadolinium oxide (e.g. removing ca. 1L from a 1000L reaction volume or equivalent). This volume fraction is then conveniently used for the addition of step (iii). This approach obviates the need to make up multiple solutions, and/or carry out multiple calculations to correct for purity or water content.

The method of the first aspect is suitable for carrying out on a laboratory, pilot plant or industrial manufacture scale. The method is particularly suitable for kilogramme scale production from 1 kg to 800 kg, preferably 100 kg to 650 kg scale.

Preferred Embodiments

In the method of the first aspect, the excess of $Gd_2O_3$ of step (i) options (a), (b) and (c) is in the range 0.001 to 5, more preferably 0.01 to 1, most preferably 0.05 to 0.5 mol/mol %.0.05 to 5 mol/mol %.

The lowest levels within this range (ca. 0.001 to 0.01 mol %) of excess gadolinium metal can be achieved by incremental addition of aliquots of gadolinium until a positive test for the presence of free gadolinium ions is observed. Such "spot tests" give a yes/no answer to the presence/absence question, but do not provide information on the concentration of free gadolinium. The spot tests can be carried out using an Arsenazo dye, as is known in the art. Alternatively, the excess gadolinium can be determined by xylenol orange assay or Arsenazo II assay as is known in the art [Barge et al, Contrast Med. Mol. Imaging, 1, 184-188 (2006) and Hvattum et al, J. Pharm. Biomed. Anal., 13(7), 927-932 (1995) respectively]. Xylenol orange and Arsenazo III are commercially available. The higher levels (>0.01 mol % up to 5 mol %), of excess gadolinium can be achieved by weighing alone.

In the method of the first aspect, the DOTA in uncomplexed form of step (iii) is preferably in an amount in the range 0.025 and 0.25, more preferably 0.08 to 0.12, most preferably 0.09 to 0.11 mol/mol % relative to the Gd-DOTA complex. The DOTA in uncomplexed form is suitably free of gadolinium metal ions, and is preferably also free of coordinated calcium, zinc and magnesium ions.

Step (ii) of the method of the first aspect preferably further comprises after the filtration, the removal of any excess $Gd^{3+}$ in solution by:
(a) contacting the filtered solution one or more times with a solid-phase bound scavenger chelator, whereby any excess $Gd^{3+}$ in solution is complexed to said scavenger chelator;
(b) separation of the solid phase from the filtered solution of step (a).

The phrase "solid-phase bound scavenger chelator" refers to a chelating agent covalently conjugated to a solid phase material insoluble in the solvent used for lanthanide complexation. The conjugated chelator complexes free metal ions in solution, and is thus capable of removing or 'scavenging' any such metal ions from solution. The scavenger chelator is chosen to be different from DOTA, and hence suitably has a lower formation constant for the gadolinium metal than DOTA, and is suitably chosen so that it cannot displace gadolinium from the Gd-DOTA metal complex. The scavenger chelator is preferably chosen such that the kinetics of capturing a free metal ion in solution are rapid. For that reason, linear (i.e. non-macrocyclic) scavenger chelators are preferred. Being bound to a solid phase, the scavenger chelator is easily separated from the solution it is in contact with by filtration, with optional washing. Suitable solid phase materials include synthetic polymers and copolymers.

The contacting of step (a) can be carried out by two principal methods, or combinations thereof. The first option is to mix the solid phase resin with the 'first solution'. Alternatively, the solid phase can be provided as a column, and the 'first solution' eluted through the column The separation of step (b) is then achieved by either filtration of the solution to remove the gadolinium-bound resin, or by collecting the eluate from the column elution respectively. Preferably, either the filtered resin or solid phase column can be washed with a suitable solvent to ensure more complete recovery of the 'second solution'. The contacting of step (a) is preferably carried out at pH 4.0 to 6, more preferably 4.5 to 5.5, with ca. pH 5 being the ideal.

The scavenger chelator preferably comprises iminodiacetic acid (IDA), EDTA or DTPA, more preferably iminodiacetic acid. A preferred solid-phase bound scavenger chelator is Chelex® 100, which is a styrene divinylbenzene copolymer, having conjugated thereto the chelator IDA. Chelex® 100 is commercially available as either the sodium or ammonium salt from Bio-Rad Laboratories and other suppliers. The commercial supplier provides information on suitable amounts of resin to use for a given amount of metal to remove. At neutral pH, Chelex functions as a cation exchange resin, so has no affinity for gadolinium metal complexes which are negatively charged such as $Gd(DOTA)^-$. That has the advantage that there is minimal non-specific binding of such complexes to the solid phase, and hence minimal impact on yield.

The scavenger chelator is preferably present as the meglumine salt of said scavenger chelator. Such materials can be prepared by conventional ion exchange chromatography techniques, to change the counter-ion (e.g. the sodium or ammonium salts of Chelex®-100), by incubation or elution with excess meglumine solution. The solid phase may then optionally be dried before use. Alternatively, the megluminium scavenger resin could be generated in situ, by adding the protonated form of the resin (obtained by washing e.g. commercial Chelex with a strong acid in a similar procedure as in Example 1). The hydroxonium Chelex resin will then form the corresponding megluminium form in situ in the complexation reaction, containing meglumine Such meglumine resins have the particular advantage that, when preparing Gd-DOTA meglumine salt, the sodium ion/salt content of the product is reduced. Thus, the counter-ion of the scavenger chelate (IDA) in the commercial Chelex® resin is sodium, and hence for every gadolinium ion that is captured, three sodium ions are released into the reaction mixture. To avoid sodium contamination, the Chelex® resin can be prepared so that all sodium ions are exchanged for megluminium ions. Consequently, when a gadolinium ion is captured by the scavenger resin, three megluminium ions are released.

After use, the scavenger chelate resin having bound metal ions may optionally be regenerated for subsequent re-use by treatment with an excess of meglumine or other counter-ion. For Chelex, standard regeneration methods are described in the instruction manual provided by the commercial supplier. The complete removal of gadolinium would be determined by ICP-AES or ICP-MS of the eluate after aqueous acidic washes of the resin, or by the 'spot-tests referred to above.

The gadolinium complexation process of step (i) is typically multistep in nature. Complexation occurs over a wide pH range, but each step of the multistep process has optimum pH ranges. Control of the reaction conditions, including pH is used in options (a), (b) (c) of step (i). A low pH (pH ca. 2) is optimal to dissolve all the $Gd_2O_3$ to give free gadolinium ions in solution. At this low pH, the carboxylate groups of DOTA are, however, unable to fully complex all the gadolinium ions because the carboxylate groups are partially protonated. At somewhat higher pH (ca. pH 4 to 5) formation of the carboxylate anion is favoured, which in turn favours metal complexation. The initial Gd-DOTA complex formed is actually bis-protonated, then slowly matures to give the final Gd-DOTA complex of high thermodynamic (and kinetic) stability [Moreau et al, Chem. Eur. J., 10(20), 5218-32 (2004)]. The maturation process is favoured by a higher pH and heating (typically a few hours at ca. pH 5 with heating).

The addition of step (iii) is preferably carried out by first neutralising to neutral pH (ca. pH 7.0-7.4), before addition of the excess DOTA. This neutralisation is preferably carried out using meglumine.

DOTA is commercially available from a range of suppliers. DOTA can also be synthesised by the method of Desreux [Inorg. Chem., 19, 1319-1324 (1980)] or Toth et al [Inorg. Chem., 33, 4070-4076 (1994)]. Further details on macrocyclic chelator syntheses are given by Kotel et al [Chapter 3 pages 83-155 in *The Chemistry of Contrast Agents in Medical Magnetic Resonance Imaging*, 2$^{nd}$ Edition, A. Merbach, L. Helm & E. Toth (Eds), Wiley (2013)].

Meglumine (N-methylglucamine) is commercially available from a range of suppliers. Preferably, pharmaceutical grade material is used.

In a second aspect, the present invention provides a method of preparation of an MRI contrast agent which comprises:
  (a) carrying out the method of the first aspect to obtain the liquid pharmaceutical formulation as defined therein;
  (b) optionally diluting the liquid pharmaceutical formulation from step (a) with a biocompatible carrier;
  (c) dispensing the formulation from step (b) into pharmaceutically acceptable containers or syringes to give dispensed containers or syringes;
  (d) either carrying out steps (a)-(c) under aseptic manufacture conditions, or terminal sterilisation of the dispensed containers or syringes from step (c) to give the MRI contrast agent in said pharmaceutically acceptable containers or syringes in a form suitable for mammalian administration.

Preferred embodiments of the liquid pharmaceutical formulation and method of step (a) in the second aspect are as described in the first aspect (above).

The term "contrast agent" has its' conventional meaning in the field of in vivo medical imaging, and refers to an agent in a form suitable for mammalian administration, which assists in providing clearer images in the region or organ of interest than could be obtained by imaging the subject alone.

An "MRI contrast agent" is typically a paramagnetic or ferromagnetic substance, suitable for mammalian administration, which shortens the T1 and/or T2 relaxation time of the relevant nuclei (e.g. $^1$H for $^1$H NMR) in the region of interest for imaging within the subject.

By the term "subject" is meant a mammal in vivo, preferably the intact mammalian body in vivo, and more preferably a living human subject. By the phrase "in a form suitable for mammalian administration" is meant a composition which is sterile, pyrogen-free, lacks compounds which produce toxic or adverse effects, and is formulated at a biocompatible pH (approximately pH 4.0 to 10.5). Such compositions lack particulates which could risk causing emboli in vivo, and are formulated so that precipitation does not occur on contact with biological fluids (e.g. blood). Such compositions also contain only biologically compatible excipients, and are preferably isotonic.

As with other in vivo imaging agents, the contrast agent is designed to have minimal pharmacological effect on the mammalian subject to be imaged. Preferably, the contrast agent can be administered to the mammalian body in a minimally invasive manner, i.e. without a substantial health risk to the mammalian subject when carried out under professional medical expertise. Such minimally invasive administration is preferably intravenous administration into a peripheral vein of said subject, without the need for local or general anaesthetic.

By the term "biocompatible carrier" is meant a fluid, especially a liquid, such that the composition is physiologically tolerable, i.e. can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is isotonic); an aqueous buffer solution comprising a biocompatible buffering agent (e.g. phosphate buffer); an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like). Preferably the biocompatible carrier is pyrogen-free water for injection (WFI), isotonic saline or phosphate buffer.

The phrase "aseptic manufacture" refers to carrying out the relevant process steps under aseptic manufacture, i.e. apyrogenic conditions, e.g. in a clean-room environment. The terms "sterilising" or "sterilisation" have their conventional meaning, and refer to a process of destruction of micro-organisms, to obtain a sterile, pyrogen-free composition. The phrase "terminal sterilisation" has its conventional meaning, and refers to carrying out the preceding steps to GMP (Good Manufacturing Practice), but carrying out the sterilisation step as late as possible in the overall process. The components and reagents can be sterilised by methods known in the art, including: sterile filtration, terminal sterilisation using e.g. gamma-irradiation, autoclaving, dry heat or chemical treatment (e.g. with ethylene oxide) or combinations thereof. The term "autoclaving" has its' conventional meaning, and refers to one particular method of sterilisation which uses superheated steam to sterilise. Autoclaving and other sterilisation methods are described in *Achieving Sterility in Medical and Pharmaceutical Products*, N. Halls (CRC Press, 1994). In the method of the second aspect, terminal sterilisation is preferred. A preferred method of terminal sterilisation is autoclaving.

The term "dispensed container or syringe" refers to a charged container, i.e. a container into which has been dispensed an aliquot of the composition, i.e. a dispensed vial.

Suitable containers, vials and closures and syringes for use in the method of the second aspect are pharmaceutical grade and are widely available commercially. The invention is illustrated by the non-limiting Examples detailed below. Example 1 provides the preparation of a meglumine scavenger chelator resin. Example 2 provides a HPLC-CAD method capable of analysing Gd-DOTA, free DOTA and meglumine in a mixture of such components.

Example 3 provides the preparation of the Gd-DOTA complex, with removal of excess gadolinium according to the methodology of the present invention.

Abbreviations

DOTA: 1,4,7,10-tetraazacyclododecane-1,4,7,10-tetraacetic acid;
DTPA: diethylenetriamine-pentaaacetic acid;
EDTA: ethylenediamine-tetraacetic acid;
GMP: Good Manufacturing Practice;
HPLC: High Performance Liquid Chromatography;
HPLC-CAD: HPLC Charged Aerosol Detector;
ICP-AES: Inductively Coupled Plasma Atomic Emission Spectroscopy
ICP-MS: Inductively Coupled Plasma Mass Spectrometry;
MeCN: acetonitrile;
Min: minutes;
MRI: Magnetic Resonance Imaging;
WFI: water for injection.

EXAMPLE 1

Preparation of Megluminized Chelex® Resin ("M$^{eg}$-Chelex")

Chelex-100 resin (Sigma-Aldrich; 100 g) on a sintered glass filter was treated with 1M HCl (1L) in 4 portions over 4 h. The resin was then washed with water until the eluent was pH 6.5, and a solution of meglumine (10 g) in water (400 mL) was equilibrated with the resin over a period of 1h. The resin was again washed with water to pH 8, filtered and dried under vacuum for a minute to give the moist resin, and used in this form ("M$^{eg}$-Chelex").

EXAMPLE 2

HPLC-CAD Method: DOTA Determination in GdDOTA-Meglumine Solution

Detector: ESA Corona, Charged Aerosol Detector;
Column: SeQuant ZIC-pHILIC (5 μm, 150*4.6 mm).
Sample preparation: to 20 μL (ca 0.5M) reaction mixture was added Zn(OAc)$_2$ (10 μL., 10 mg/mL) then water (270 μL) followed by MeCN (700 μL)*.
Injection volume: 20 μL;
Mobile phase: 100 mM ammonium acetate (A), Acetonitrile (B).
The column was conditioned with an initial composition (of 15:85 A:B) at a flow rate of 1 mL/min for at least five minutes prior to sample injection.

Gradient:

| | Time (min) | Flow Rate (mL/min) | % A | % B | Curve |
|---|---|---|---|---|---|
| 1. | initial | 1.00 | 15.0 | 85.0 | |
| 2. | 50.00 | 1.00 | 33.0 | 66.0 | 6 | where curve 6 refers to a linear gradient.
The following retention times were observed:

| | Retention time (min) |
|---|---|
| Meglumine | 21.3 |
| GdDOTA | 23.2 |
| ZnDOTA* | 28.1. |

*DOTA was analysed indirectly as the ZnDOTA complex.

EXAMPLE 3

Preparation of Gd-DOTA-Meglumine Solution with Gadolinium Ion Removal

Meglumine (0.749 g, 4.00 mmol), DOTA (1.615 g 4.00 mmol), gadolinium oxide (0.749 g 2.04 mmol) and water (8.0 g) were combined in a flask and stirred at 60° C. overnight.

This gave a mixture where the solution was distinctly turbid. The mixture was filtered with a syringe filter (Pall Acrodisc 25mm with 0.45μ PVDF membrane) to yield a clear solution having a pH ~9. No free gadolinium was detected using Arzenazo indicator [Hvatum et al, J. Pharm. Biomed. Anal., 13(7), 927-932 (1995)]. The limit of detection is <9.4 μg/mL or <0.06 mM. Arzenazo III dye is commercially available.

The invention claimed is:

1. A method for preparing a liquid pharmaceutical formulation comprising a meglumine salt of the metal complex Gd-DOTA, together with DOTA in uncomplexed form in an amount in the range 0.002 and 0.4 mol/mol % of said Gd-DOTA complex, said method comprising:
   (i) preparing a first Gd-DOTA solution comprising the Gd-DOTA meglumine salt and an excess of undissolved Gd$_2$O$_3$;
   (ii) filtering the first Gd-DOTA solution from step (i) to remove the excess undissolved Gd$_2$O$_3$, giving a second Gd-DOTA solution; and
   (iii) adding free DOTA to the second Gd-DOTA solution from step (ii) so that the level of free DOTA makes up an amount in the range 0.002 and 0.4 mol/mol % of said Gd-DOTA complex;
   wherein the free DOTA is free of coordinated metal ions.

2. The method of claim 1, wherein step (i) comprises one of the following processes (a), (b), or (c):
   (a) reacting an aqueous solution of a 1:1 molar ratio of DOTA and meglumine with an excess of Gd$_2$O$_3$, whereby all the DOTA reacts to give Gd-DOTA; or
   (b) reacting an aqueous solution of DOTA with a deficiency of Gd$_2$O$_3$ at pH 2.0 to 6.0 whereby all the gadolinium reacts to give Gd-DOTA, followed by the addition of meglumine to raise the pH to 6.5 to 8.0, and then addition of an excess of Gd$_2$O$_3$; or
   (c) reacting an aqueous solution of DOTA with an excess of meglumine at pH 6.5 to 8.0, with an excess of Gd$_2$O$_3$, whereby all the DOTA reacts to give Gd-DOTA.

3. The method of claim 2, wherein the excess of $Gd_2O_3$ of step (a), (b), or (c) is in the range 0.05 to 5 mol/mol %.

4. The method of claim 1, wherein the free DOTA of step (iii) is in the range 0.025 and 0.25 mol/mol %.

5. The method of claim 1, wherein the free DOTA is free of lanthanide, calcium, sodium, zinc and magnesium ions.

6. The method of claim 1, wherein step (ii) further comprises after the filtration, the removal of any excess $Gd^{3+}$ in solution by:
   (a) contacting the filtered solution one or more times with a solid-phase bound scavenger chelator, whereby any excess $Gd^{3+}$ in solution is complexed to said scavenger chelator;
   (b) separation of the solid phase from the filtered solution of step (a).

7. The method of claim 6, wherein the solid-phase bound scavenger chelator is present as the meglumine salt of said scavenger chelator.

8. The method of claim 6, wherein the scavenger chelator comprises iminodiacetic acid.

9. The method of claim 2, wherein the gadolinium complexation of step (i)(a) or (i)(b) is carried out at 50 to 80° C.

10. A method of preparation of an MRI contrast agent, the method comprising:
   (a) carrying out the method of claim 1 to obtain the liquid pharmaceutical formulation as defined therein;
   (b) optionally diluting the liquid pharmaceutical formulation from step (a) with a biocompatible medium;
   (c) dispensing the formulation from step (b) into pharmaceutically acceptable containers or syringes to give dispensed containers or syringes;
   (d) either carrying out steps (a)-(c) under aseptic manufacture conditions, or terminal sterilization of the dispensed containers or syringes from step (c) to give the MRI contrast agent in said pharmaceutically acceptable containers or syringes in a form suitable for mammalian administration.

11. The method of claim 10, wherein terminal sterilization is used.

* * * * *